US 8,491,550 B2

(12) United States Patent
Ramella et al.

(10) Patent No.: US 8,491,550 B2
(45) Date of Patent: Jul. 23, 2013

(54) DRAINAGE TUBE UNIT

(75) Inventors: Ivo Ramella, Ebikon (CH); Fabian Joder, Baar (CH)

(73) Assignee: Medela Holding AG, Baar (CH)

( * ) Notice: Subject to any disclaimer, the term of this patent is extended or adjusted under 35 U.S.C. 154(b) by 753 days.

(21) Appl. No.: 12/598,841

(22) PCT Filed: May 16, 2008

(86) PCT No.: PCT/CH2008/000224
§ 371 (c)(1),
(2), (4) Date: Nov. 4, 2009

(87) PCT Pub. No.: WO2008/141470
PCT Pub. Date: Nov. 27, 2008

(65) Prior Publication Data
US 2010/0094234 A1    Apr. 15, 2010

(30) Foreign Application Priority Data
May 22, 2007    (CH) ........................................ 0823/07

(51) Int. Cl.
*A61M 1/00*    (2006.01)
(52) U.S. Cl.
USPC ............................ 604/319; 604/533; 604/542
(58) Field of Classification Search
USPC .................. 604/22, 26, 28, 119, 319
See application file for complete search history.

(56) References Cited

U.S. PATENT DOCUMENTS

| 5,029,580 A | 7/1991 | Radford et al. |
| 5,134,996 A | 8/1992 | Bell |
| 5,140,983 A | 8/1992 | Jinotti |
| 5,328,456 A | 7/1994 | Horiguchi et al. |
| 5,582,588 A | 12/1996 | Sakurai et al. |
| 5,738,656 A | 4/1998 | Wagner |
| 6,261,276 B1 * | 7/2001 | Reitsma ........................ 604/319 |

(Continued)

FOREIGN PATENT DOCUMENTS

| DE | 19913713 A1 | 9/2000 |
| EP | 0466334 B1 | 1/1992 |

(Continued)

OTHER PUBLICATIONS

International Preliminary Report on Patentability for corresponding PCT application No. PCT/CH2008/000224 (10 pages).

*Primary Examiner* — Melanie Hand
(74) *Attorney, Agent, or Firm* — McDonnell Boehnen Hulbert & Berghoff LLP

(57) ABSTRACT

A drainage tube unit for aspirating body fluids by means of a suction pump comprises a drainage tube (10) for aspirating the body fluids and at least one service tube (11), each of them with a patient-side end and a pump-side end, the patient-side ends of the drainage tube (10) and of the service tube (11) being arranged in a common patient-side attachment part (3), and the pump-side ends of the drainage tube (10) and of the service tube (11) being arranged in a common pump-side attachment part (2). The ends of the drainage tube (10) extend separate from the ends of the service tube (11), the patient-side ends opening into a drainage channel (37) and a service channel (35) of the patient-side attachment part (3), and the pump-side ends opening into a drainage channel (24) and a service channel (25) of the pump-side attachment part (2). The drainage tube unit according to the invention is inexpensive to produce and is easy and safe to use.

22 Claims, 3 Drawing Sheets

U.S. PATENT DOCUMENTS

| | | |
|---|---|---|
| 6,394,996 B1 | 5/2002 | Lawrence et al. |
| 6,626,827 B1 | 9/2003 | Felix et al. |
| 2007/0167906 A1 | 7/2007 | Alexandre et al. |

FOREIGN PATENT DOCUMENTS

| | | |
|---|---|---|
| EP | 0861668 B1 | 9/1998 |
| JP | 1-19959 | 6/1989 |
| JP | 2001-503649 | 3/2001 |
| JP | 2001-507971 | 6/2001 |
| RU | 2309769 C2 | 11/2007 |
| WO | 98/30270 | 7/1998 |
| WO | 01/24846 A1 | 4/2001 |
| WO | 03/016719 | 2/2003 |
| WO | 2005/061025 A1 | 7/2005 |
| WO | 2007/128156 A2 | 11/2007 |

* cited by examiner

DRAINAGE TUBE UNIT

TECHNICAL FIELD

The invention relates to a drainage tube unit and to attachment parts.

PRIOR ART

Drainage pump systems are used to aspirate body liquids and fluids in the medical field, for example during or after surgical interventions, but also in wound drainage, thorax drainage or liposuction. These drainage pump systems usually have a suction pump, one or more fluid collection containers and a drainage tube connection between patient and fluid collection container. The fluid collection container can be secured releasably on the housing of the drainage pump or can be connected to the pump via a vacuum tube.

With an underpressure being generated in the fluid collection container by means of the suction pump or vacuum pump, the fluid or secretion from a cavity in the patient is aspirated through the drainage tube and into the collection container and is collected therein. Filters arranged on the pump-side outlet of the collection container protect the suction pump from contamination by the aspirated fluid. A fluid collection container of this kind with a rigid cover and with a flexible bag secured thereon is known, for example, from EP 0 861 668 and WO 01/24846.

EP 0 466 334 discloses a drainage line with a drainage catheter and an airtight sleeve surrounding the catheter. At both of its ends, the catheter is connected to an attachment part. An connector for a gas analyzer is provided on the patient-side attachment part.

In addition to the drainage line, it is also known to run a service line from the pump to the patient. For example, U.S. Pat. No. 5,738,656 uses a double-lumen tube, one lumen forming the drainage line, and the second lumen being an air conduit which, at the patient-side end, opens into the drainage line. In this way, air or gas can be fed into the patient cavity to be aspirated, and the cavity can thus be flushed. This lumen can additionally be used as a measurement line for determining flow differences or pressure differences. In this way, the drainage procedure can be optimally monitored and also automatically controlled.

In WO 05/061025, a service line connected to the patient-side end of the drainage tube is used to flush the drainage line, in order to avoid or to eliminate occlusion of the line by aspirated clots or tissues.

U.S. Pat. No. 6,626,827 describes a drainage tube unit with two tubes, which drainage tube unit has a y-shaped attachment part at the pump-side end. At the patient-side end, the two tubes open into two independent attachment parts.

U.S. Pat. No. 5,029,580 discloses a drainage tube unit with a double-lumen tube, which contains a drainage line and an air delivery line. At the patient-side end, the tube has internal through-openings that connect the two lines to each other. At its ends, this tube is provided with a pump-side attachment part and a patient-side attachment part. Further connection possibilities are also provided in these attachment parts.

U.S. Pat. No. 5,134,996 discloses a multi-lumen drainage tube which is surrounded by a sleeve and which, at its two ends, is provided with attachment parts.

Although these connectors, by virtue of their attachment parts, avoid incorrect manipulations, they nevertheless have a relatively complicated structure, particularly since they are composed of a plurality of individual parts. In addition, they can also only be used with a double-lumen catheter tube, in particular only with a tube that has a specially designed patient-side end. However, since these drainage tube units cannot be used more than once and are discarded as disposable parts after one use, they have to be as inexpensive as possible.

DISCLOSURE OF THE INVENTION

It is an object of the invention to make available a drainage tube unit that permits safe handling and that can be produced inexpensively.

This object is achieved by a drainage tube unit with the features of Patent Claim 1.

The drainage tube unit according to the invention for aspirating body fluids by means of a suction pump comprises a drainage tube for aspirating the body fluids and at least one service tube, each of them with a patient-side end and a pump-side end, the patient-side ends of the drainage tube and of the service tube being arranged in a common patient-side attachment part, and the pump-side ends of the drainage tube and of the service tube being arranged in a common pump-side attachment part. The pump-side attachment part is designed to be plugged into an associated suction device. The ends of the drainage tube extend separate from the ends of the service tube, the patient-side ends opening into a drainage channel and a service channel of the patient-side attachment part, and the pump-side ends opening into a drainage channel and a service channel of the pump-side attachment part.

According to the invention, commercially available and inexpensive single-lumen tubes can be used. The tubes can be plugged next to each other into the attachment parts. The advantage of this solution is that the tube ends can also be inserted into the attachment parts on different sides thereof, such that the attachment parts can be configured in any desired way and can be adapted to the pump and to the patient-side situation. The tubes can additionally extend parallel to each other all the way between the attachment parts, along considerable distances or not at all.

Since a ready-assembled tube unit with two end connectors or attachment parts is provided, and since attachment parts are provided on both sides, it is ensured that the tube unit is inserted correctly into the associated suction device.

These attachment parts are preferably produced inexpensively from plastic by an injection-moulding process and, in particular, are designed in one piece.

The patient-side attachment part can in particular be made in one piece by the injection-moulding process if the connection channel is open to the outside on one side and is only subsequently closed.

If the closure is obtained by means of a stopper, it is advantageous for the latter also to be injection-moulded in one piece with the rest of the attachment part. It can thus be pressed automatically into the opening of the connection channel before the attachment part is ejected from the injection mould.

A further object of the invention is to create a drainage tube unit that can be produced inexpensively. This object is achieved by a drainage tube unit with the features of Patent Claim 22.

The drainage tube unit according to the invention for aspirating body fluids by means of a suction pump comprises a drainage tube for aspirating the body fluids and at least one service tube, each of them with a patient-side end and a pump-side end, the patient-side ends of the drainage tube and of the service tube being arranged in a common patient-side attachment part. The patient-side end of the drainage tube extends separate from the patient-side end of the service tube, these patient-side ends opening into a drainage channel or service channel of the patient-side attachment part, the service channel having a smaller diameter than the drainage channel, and the two channels being connected to each other via a connection channel.

Since the connection between the two lines is in the patient-side attachment part and no longer in the tube itself, it is possible to use simple, commercially available single-lumen tubes, in particular of silicone or PVC. This attachment part can also be used without a pump-side attachment part in a tube system.

In all embodiments, several lines can also be used instead of two lines, such that there is not just one service channel in each of the attachment parts, but several service channels, at least one of these channels being connected to the drainage channel at the patient side via the connection channel.

Other advantageous embodiments will become evident from the dependent patent claims.

BRIEF DESCRIPTION OF THE DRAWINGS

The subject matter of the invention is explained below on the basis of a preferred illustrative embodiment depicted in the attached drawings, in which.

WAYS OF IMPLEMENTING THE INVENTION

Figure 1:
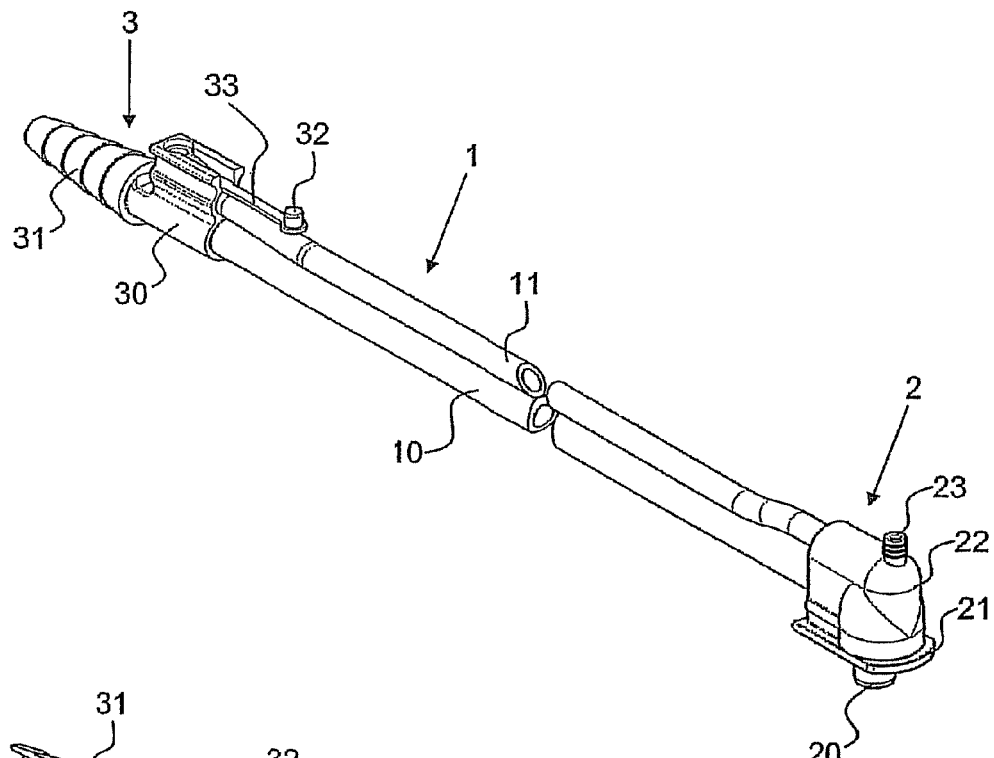
FIG. 1 shows a perspective view of a drainage tube unit according to the invention.

FIG. 1 shows the drainage tube unit according to the invention as used in the drainage aspiration devices mentioned at the outset. It is composed mainly of a tube system 1 with two or more tubes 10, 11, a pump-side attachment part 2 and a patient-side attachment part 3.

The tubes 10, 11 are preferably single-lumen tubes independent of each other. They are preferably made of silicone or PVC. They extend separate from each other at their ends. Between the ends, they can be adhesively bonded to each other, welded to each other or otherwise connected. In the figures, the tubes are not shown at their full length and are instead interrupted.

The two tubes preferably have different diameters. The thicker tube 10 forms an underpressure and drainage line for aspirating the body fluid. The thinner tube 11 forms a service line which, for example, permits the above-described or similar pressure measurement and/or cleaning of the drainage line. Both applications can be carried out jointly but one after the other if the suction unit at the pump-side end of the service line has a valve which is closed for the underpressure measurement during the aspiration procedure. During the cleaning mode, however, the valve is opened. The service line can also be used in other known ways. The service function serves to support the drainage function and can, for example, include the aforementioned functions according to the prior art.

The two tubes 10, 11 preferably extend parallel to each other along approximately the entire length, and their ends in particular open out in parallel, but spaced apart from each other, into the respective attachment parts or elements 2, 3. Spaced apart means that they can bear on each other or that they can leave a space free between them. At least in one of the two parts, they protrude inwards on the same side of the attachment part. The ends are inserted into the attachment parts 2, 3, adhesively bonded in them or otherwise secured.

The pump-side attachment 2, which is designed as an end connector to be plugged into the associated suction device, will first be described below. Pump-side in this context, however, simply means remote from the patient. Instead of being in a pump housing, the attachment part can instead also be arranged in a fluid collection container or other unit remote from the patient. Therefore, where the term pump-side is used below and in the patent claims, this also means the container side. Where the term suction device is used below and in the patent claims, this means, among other things, the pump housing or the fluid collection container.

The pump-side attachment part 2 is preferably made of plastic by injection moulding, and it is preferably designed in one piece.

Figure 4:
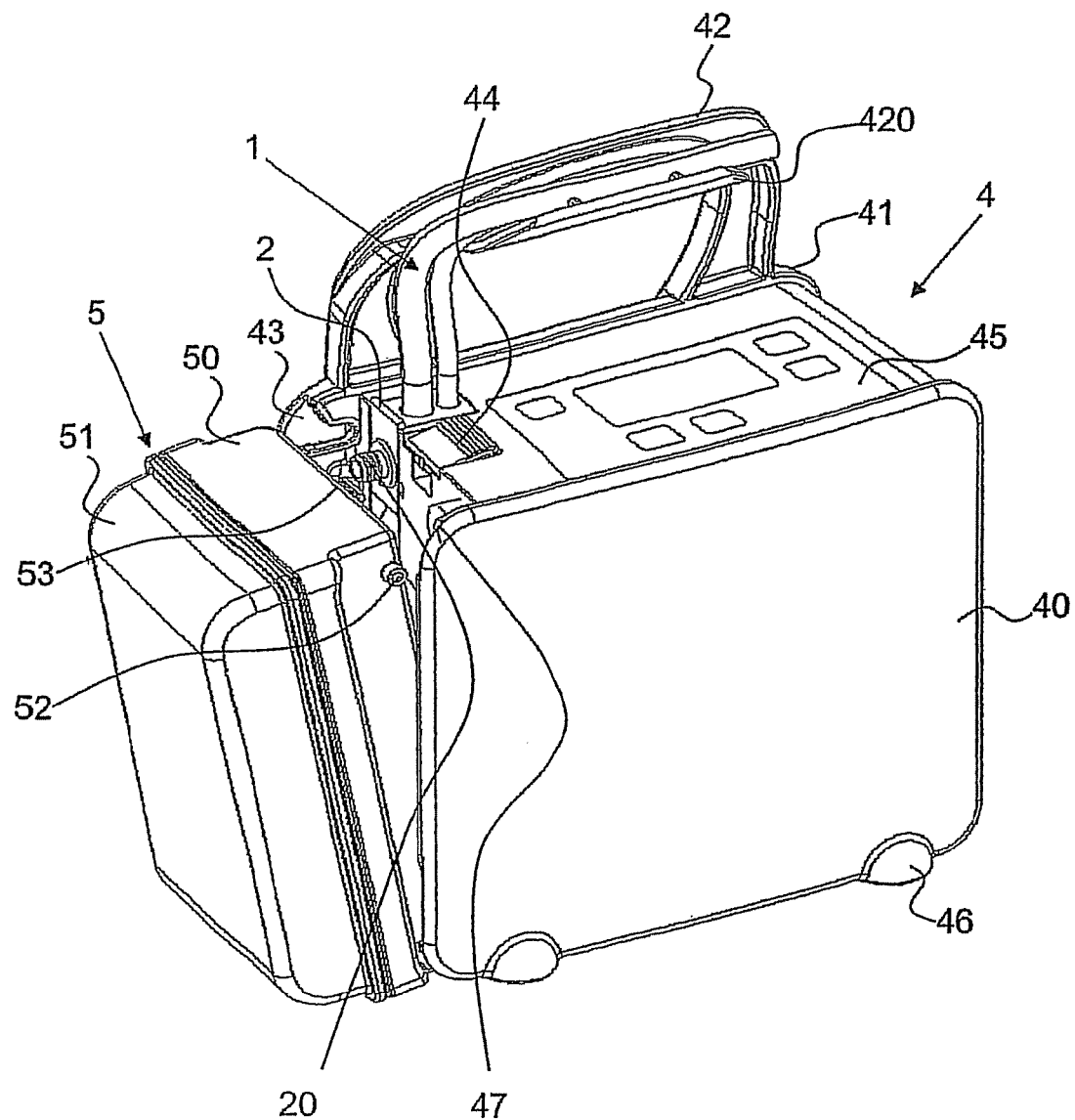
FIG. 4 shows a perspective view of a drainage pump device with a pump-side attachment part of the drainage tube unit according to the invention.

It has a substantially cuboid main body 2, which is here provided with a peripheral flange 21. With this flange 21, the part 2 can be introduced with a form fit into a corresponding recess of the pump housing and held therein, as is shown in FIG. 4.

Figure 2:
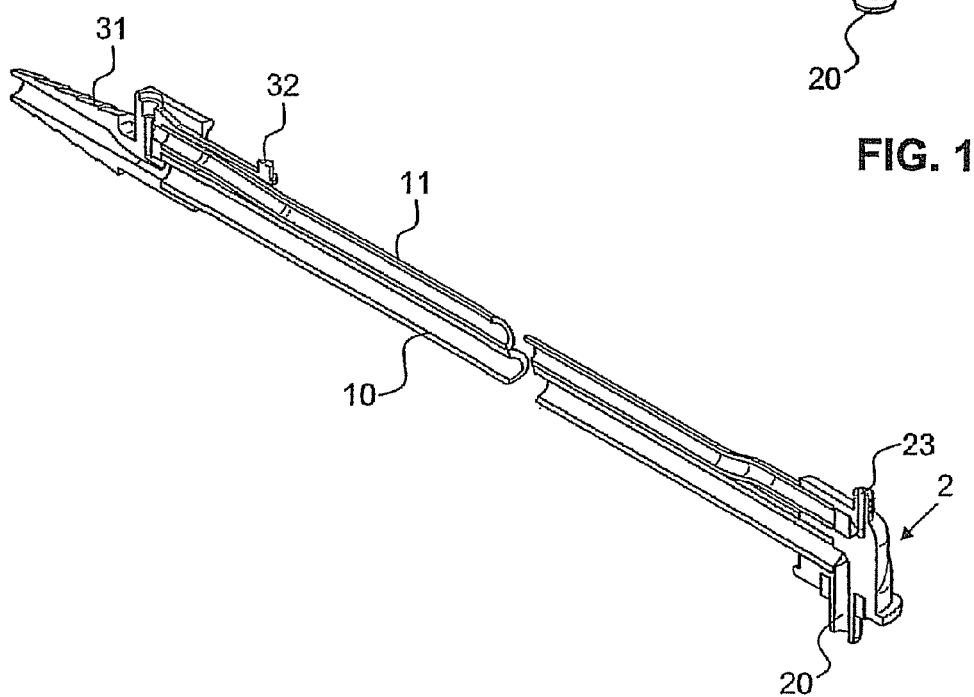
FIG. 2 shows a perspective view through a drainage tube unit according to FIG. 1 when sectioned in the longitudinal direction.
Figure 3:
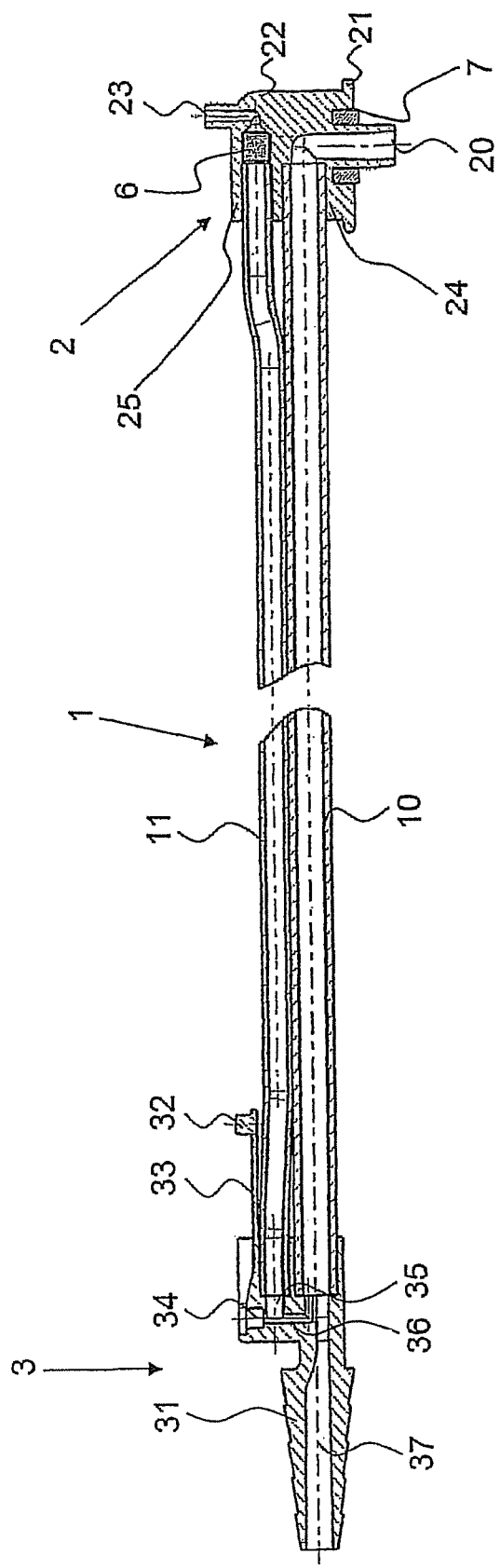
FIG. 3 shows a longitudinal section through the drainage tube unit according to FIG. 1.

As can be seen from FIGS. 2 and 3, the attachment part 2 has two channels 24, 25, and the pump-side ends of the drainage and service tubes 10, 11 are inserted into their mouth openings that lie parallel to each other but spaced apart from each other.

A filter 6 is arranged in the pump-side service channel 25. This, for example, is a hydrophobic filter and/or a bacterial filter. The service channel 25 then narrows and bends off at right angles with respect to the mouth. It ends in a service inlet 23 that protrudes in the form of a connector piece from the main body 22. This service inlet 23 serves for connection to a service unit of the suction device.

The pump-side drainage channel 24 also bends off at right angles with respect to its mouth and likewise ends in a connector piece, the pump-side drainage outlet 20, protruding from the main body 22. This outlet 20 serves for connection to a fluid collection container. The outlet 20 is here arranged at right angles to the mouth of the tube 10, but it can also be arranged on a different side of the main body 22 than the mouth side. The same applies for the service inlet 23 in relation to the mouth of the service tube 10.

The aspirated fluid passes through the drainage outlet into the container. To ensure leaktightness, a peripheral groove can be provided round the drainage outlet 20 in the main body 22. The groove can be provided with a sealing ring. The drainage outlet 20 is preferably arranged on a side of the main body 22 that lies opposite the side with the service inlet 23.

The patient-side attachment part 3 is likewise preferably made of plastic by injection moulding. It too is preferably designed in one piece.

It has a main body 30 with two mouths for the patient-side ends of the drainage tube 10 and of the service tube 11, which mouths extend in parallel to each other but spaced apart from each other. A patient-side drainage inlet 31, formed integrally on this main body 30, has a conical shape and is provided with steps and narrows towards its free open end. It has a Christmas tree shape in cross section. The drainage inlet 31 preferably extends approximately in axial alignment with the mouth of the patient-side end of the drainage tube 10, such that the patient-side drainage channel 37 in the interior of the attachment part extends approximately in a straight line.

The patient-side end of the service tube 11 is plugged into a mouth of a patient-side service channel 35, which preferably has a smaller diameter than the drainage channel 37. The channel 37, also like all the other channels described, has a step that serves as an abutment for the tube 11. The mouths described above are understood as extending as far as these steps.

The service channel 23 ends in the main body 30 and there opens into a connection channel 36, which is preferably perpendicular to the service channel 23. The connection channel 36 has the same diameter as or preferably a smaller diameter than the service channel 35. It terminates at one end in a right-angled bend in the drainage channel 37, preferably at the step to the mouth. Its other end forms an opening 34 to the outside, which opening 34 is preferably arranged perpendicular to the mouths in the main body 30.

This opening 34 is closed by a sealing closure 32, in this case a stopper. In the figure, it is shown still in the open state, being preferably already closed in this configuration. In fact it is preferably already closed on ejection from the injection moulding machine, that is to say long before the tubes 10, 11 are secured.

The sealing closure 32 is preferably produced in one piece with the rest of the attachment part 3 and, as is shown, is therefore connected to the main body 30 via a band 33. This opening permits the one-piece production of this attachment part.

FIG. 4 shows a drainage pump device with which the drainage tube unit according to the invention is preferably used. It serves to aspirate body liquids or fluids in the medical field, for example during or after surgical interventions, but also for wound drainage, thorax drainage, or for liposuction.

However, the tube unit can also be used with other drainage pump devices. It is preferable, but not essential, that the fluid collection container and the pump unit can be connected to each other by means of the pump-side attachment part without further intermediate lines.

The drainage pump device shown here has a pump housing 4 which accommodates a vacuum pump or suction pump and electronics for operating the pump and for evaluating measured values obtained by way of the service tube.

The pump housing 4 preferably has a cuboid shape with a front wall 40, a rear wall 41, a handle 42 and feet 46. On an upper face of the housing 4, there is an operating panel 45 for operating the pump, preferably with a display.

The front wall 40 and the rear wall 41 jut out at one side and form a recess for a fluid collection container 5. This fluid collection container 5 is preferably composed of two container halves 50, 51 and is made of a transparent plastic.

The container 5 can be secured releasably on the pump housing 4, preferably being swivelled in and engaged in this position. For this purpose, the front wall 40 and the rear wall 41 of the pump housing 4 have upper and lower slide guides in which upper and lower securing pins 52 of the container 5 engage. Only one upper pin can be seen in the figure. The lower pins are already engaged, as can be seen from the oblique position of the container 5.

The container 5 has a hook 53 which is directed towards the housing 4 and in which a flip switch 44 of the housing 4 engages with a corresponding projection. In this way, the container 5 is fixed releasably on the housing 4.

Facing the container 5, a suction connector 47 is provided on the housing 4. It has the shape of a nozzle, which engages in a corresponding opening of the container 5. In this way, an underpressure can be generated in the container 5 by means of the suction pump.

The housing 4 also has a substantially cuboid recess into which the pump-side attachment part 2 of the drainage tube unit according to the invention can be inserted and is held releasably therein with a form fit. The container-side drainage outlet 20 of the attachment part 2 is oriented towards the container 5. Through it the aspirated fluid passes into the container 5.

At right angles thereto, the tube system 1 with the two tubes 10, 11 opens into the pump-side attachment part 2. The tube system 1 in this example is routed along the housing 4 in a channel 420 arranged on the handle 42.

The service inlet 23, which protrudes into the pump housing 4 and is connected to a corresponding control and/or evaluation unit, cannot be seen.

The drainage tube unit according to the invention can be produced inexpensively and is easy and safe to use.

LIST OF REFERENCE NUMBERS 1 tube system
10 drainage tube
11 service tube
2 pump-side attachment part
20 pump-side drainage outlet
21 flange
22 main body
23 pump-side service inlet
24 pump-side drainage channel
25 pump-side service channel
3 patient-side attachment part
30 main body
31 patient-side drainage inlet
32 sealing cover
33 band
34 opening
35 patient-side service channel
36 connection channel
37 patient-side drainage channel
4 pump housing
40 front wall
41 rear wall
42 handle
420 channel
43 slide guide
44 flip switch
45 operating panel
46 foot
47 suction connector
5 fluid collection container
50 first half of container
51 second half of container
52 securing pin
53 hook
6 filter
7 sealing ring

The invention claimed is:

1. A drainage tube unit for aspirating body fluids by means of a suction pump, the tube unit comprising a drainage tube for aspirating the body fluids and at least one service tube, each of the drainage tube and the at least one service tube having a patient-side end and a pump-side end, the patient-side ends of the drainage tube and of the service tube being arranged in a common patient-side attachment part, and the pump-side ends of the drainage tube and of the service tube being arranged in a common pump-side attachment par, the pump-side attachment part being designed to be plugged into an associated suction device, wherein the ends of the drainage tube extend separate from the ends of the service tube, and the patient-side ends open into a drainage channel and a service channel of the patient-side attachment part, and the pump-side ends open into a drainage channel and a service channel of the pump-side attachment part, wherein the drainage channel of the pump-side attachment part has a drainage mouth for receiving the pump-side end of the drainage tube, and a drainage outlet, the drainage outlet being arranged on a different side than the drainage mouth, wherein the pump-side attachment part has a substantially cuboid shape, and wherein the drainage outlet is arranged substantially at a right angle to the drainage mouth.

2. The drainage tube unit according to claim 1, in which the pump-side attachment part and/or the patient-side attachment part are designed in one piece.

3. The drainage tube unit according to claim 1, in which the patient-side and pump-side ends of the drainage tube and service tube extend parallel to each other as they open into the attachment parts.

4. The drainage tube unit according to claim 1, in which the drainage tube and the at least one service tube are two separate single-lumen tubes.

5. The drainage tube unit according to claim 1, wherein the drainage tube and the at least one service tube open into at least one of said attachment parts on the same side of this attachment part.

6. The drainage tube unit according to claim 1, in which the service channel of the pump-side attachment part has a service mouth for receiving the pump-side end of the service tube, and a service inlet, the service inlet being arranged on a different end than the service mouth.

7. The drainage tube unit according to claim 6, in which the service inlet is arranged substantially at a right angle to the service mouth.

8. The drainage tube unit according to claim 6, in which the service inlet is arranged on a side of the pump-side attachment part lying opposite the drainage outlet.

9. The drainage tube unit according to claim 1, in which a filter is arranged in the service channel of the pump-side attachment part.

10. The drainage tube unit according to claim 1, in which the pump-side attachment part is designed such that it is able to be held releasably in the suction pump with a form fit.

11. The drainage tube unit according to claim 1, in which the drainage channel and the service channel of the patient-side attachment part are connected to each other via a connection channel.

12. The drainage tube unit according to claim 11, in which a first end of the connection channel leads into the drainage channel and a second end leads to the outside, the second end being able to be closed with a sealing cover.

13. The drainage tube unit according to claim 12, in which the sealing cover is formed integrally on the patient-side attachment part.

14. The drainage tube unit according to claim 1, in which the patient-side attachment part has a main body for receiving the ends of the drainage tube and service tube, and, adjoining the main body, a patient-side drainage inlet—which has a conical shape and is designed with steps, the drainage inlet extending approximately in axial alignment with the mouth of the patient-side end of the drainage tube.

15. A patient-side attachment part for use in a drainage tube unit according to claim 1, in which the patient-side attachment part has a drainage channel with a patient-side drainage inlet and with a pump-side drainage mouth for receiving an end of a drainage tube and a pump-side service channel for receiving a service tube, the service channel of the patient-side attachment part having a smaller diameter than the drainage channel of the patient-side attachment part with a connection channel also being provided that connects the service channel of the patient-side attachment part to the drainage channel of the patient-side attachment part, wherein a first end of the connection channel leads into the drainage channel of the patient-side attachment part and a second end leads to the outside, the second end being designed such that it is able to be closed, and the patient-side attachment part is produced in one piece by injection molding.

16. A pump-side attachment part for use in a drainage tube unit according to claim 1, in which the pump-side attachment part has a main body in which a drainage channel and a service channel extend, the drainage channel having a pump-side drainage outlet, for connection to an associated suction device, and a patient-side drainage mouth for receiving a pump-side end of a drainage tube, the drainage outlet being arranged on a different side of the main body than the drainage mouth, and the service channel having a pump-side service inlet, for connection to an associated suction device, and a service mouth for receiving the pump-side end of the service tube, the service inlet being arranged on a different side of the main body than the service mouth, and the pump-side attachment part being designed to be plugged into the suction device, wherein the main body has a substantially cuboid shape, and the service inlet is arranged substantially at a right angle to the service mouth.

17. The attachment part according to claim 16, in which the drainage outlet is arranged on an opposite side from the service inlet.

18. A drainage tube unit for aspirating body fluids by means of a suction pump, the tube unit comprising a drainage tube for aspirating the body fluids and at least one service tube, each of the drainage tube and the at least one service tube having a patient-side end and a pump-side end, the patient-side ends of the drainage tube and of the service tube being arranged in a common patient-side attachment part, wherein the patient-side end of the drainage tube extends separate from the patient-side end of the service tube, and the patient-side ends open into a drainage channel or service channel of the patient-side attachment part, the service channel having a smaller diameter than the drainage channel, and the drainage channel and the service channel being connected to each other via a connection channel, wherein a first end of the connection channel leads into the drainage channel of the patient-side attachment part and a second end leads to the outside, the second end being designed such that it is able to be closed, and the patient-side attachment part is produced in one piece by injection molding.

19. A drainage tube unit for aspirating body fluids by means of a suction pump, the tube unit comprising a drainage tube for aspirating the body fluids and at least one service tube, each of the drainage tube and the at least one service tube having a patient-side end and a pump-side end, the patient-side ends of the drainage tube and of the service tube being arranged in a common patient-side attachment part, and the pump-side ends of the drainage tube and of the service tube being arranged in a common pump-side attachment part, the pump-side attachment part being designed to be plugged into an associated suction device, wherein the ends of the drainage tube extend separate from the ends of the service tube, and the patient-side ends open into a drainage channel and a service channel of the patient-side attachment part, and the pump-side ends open into a drainage channel and a service channel of the pump-side attachment part, wherein the service channel of the pump-side attachment part has a service mouth, for receiving the pump-side end of the service tube, and a service inlet, the service inlet being arranged on a different end than the service mouth, wherein the pump-side attachment part has a substantially cuboid shape, and in which the service inlet is arranged substantially at a right angle to the service mouth.

20. A drainage tube unit for aspirating body fluids by means of a suction pump, the tube unit comprising a drainage tube for aspirating the body fluids and at least one service tube, each of the drainage tube and the at least one service tube having a patient-side end and a pump-side end, the patient-side ends of the drainage tube and of the service tube being arranged in a common patient-side attachment part, and the pump-side ends of the drainage tube and of the service tube being arranged in a common pump-side attachment part, the pump-side attachment part being designed to be plugged into an associated suction device, wherein the ends of the drainage tube extend separate from the ends of the service tube, and the patient-side ends open into a drainage channel and a service channel of the patient-side attachment part, and the pump-side ends open into a drainage channel and a service channel of the pump-side attachment part, wherein the drainage channel and the service channel of the patient-side attachment part are connected to each other via a connection channel.

21. A pump-side attachment part for use in a drainage tube unit according to claim 1, in which the pump-side attachment part has a main body in which a drainage channel and a service channel extend, the drainage channel having a pump-side drainage outlet, for connection to an associated suction device, and a patient-side drainage mouth for receiving a pump-side end of a drainage tube, the drainage outlet being arranged on a different side of the main body than the drainage mouth, and the service channel having a pump-side service inlet, for connection to an associated suction device, and a service mouth for receiving the pump-side end of the service tube, the service inlet being arranged on a different side of the main body than the service mouth, and the pump-side attachment part being designed to be plugged into the suction device, wherein the drainage channel of the pump-side attachment part has a drainage mouth, for receiving the pump-side end of the drainage tube, and a drainage outlet, the drainage outlet being arranged on a different side than the drainage mouth.

22. A pump-side attachment part for use in a drainage tube unit according to claim 1, in which the pump-side attachment part has a main body in which a drainage channel and a service channel extend, the drainage channel having a pump-side drainage outlet, for connection to an associated suction device, and a patient-side drainage mouth for receiving a pump-side end of a drainage tube, the drainage outlet being arranged on a different side of the main body than the drainage mouth, and the service channel having a pump-side service inlet, for connection to an associated suction device, and a service mouth for receiving the pump-side end of the service tube, the service inlet being arranged on a different side of the main body than the service mouth, and the pump-side attachment part being designed to be plugged into the suction device, wherein the service channel of the pump-side attachment part has a service mouth, for receiving the pump-side end of the service tube, and a service inlet, the service inlet being arranged on a different end than the service mouth, and in which the service inlet is arranged substantially at a right angle to the service mouth.

* * * * *